(12) United States Patent
Vogt et al.

(10) Patent No.: US 10,667,995 B2
(45) Date of Patent: Jun. 2, 2020

(54) ORAL CARE COMPOSITIONS

(75) Inventors: Robert Vogt, Princeton Junction, NJ (US); Karsten Kohrs, Berkeley Heights, NJ (US); Shira Pilch, Highland Park, NJ (US); Najma Khan, Somerset, NJ (US); Paloma Pimenta, Staten Island, NY (US); Richard Joseph Sullivan, Atlantic Highlands, NJ (US)

(73) Assignee: Colgate-Palmolive Company, New York, NY (US)

( * ) Notice: Subject to any disclaimer, the term of this patent is extended or adjusted under 35 U.S.C. 154(b) by 127 days.

(21) Appl. No.: 13/983,370

(22) PCT Filed: Oct. 5, 2011

(86) PCT No.: PCT/US2011/054905
§ 371 (c)(1),
(2), (4) Date: Aug. 2, 2013

(87) PCT Pub. No.: WO2012/106016
PCT Pub. Date: Aug. 9, 2012

(65) Prior Publication Data
US 2013/0315845 A1 Nov. 28, 2013

Related U.S. Application Data

(60) Provisional application No. 61/439,550, filed on Feb. 4, 2011.

(51) Int. Cl.

| | | |
|---|---|---|
| *A61K 8/04* | (2006.01) | |
| *A61Q 11/00* | (2006.01) | |
| *A61K 8/24* | (2006.01) | |
| *A61K 8/21* | (2006.01) | |
| *A61K 8/44* | (2006.01) | |
| *A61K 8/73* | (2006.01) | |
| *A61K 8/46* | (2006.01) | |
| *A61K 8/90* | (2006.01) | |

(52) U.S. Cl.
CPC .............. *A61K 8/046* (2013.01); *A61K 8/442* (2013.01); *A61K 8/463* (2013.01); *A61K 8/73* (2013.01); *A61K 8/731* (2013.01); *A61K 8/90* (2013.01); *A61Q 11/00* (2013.01)

(58) Field of Classification Search
CPC ........ A61Q 11/00; A61K 8/046; A61K 8/442; A61K 8/90; A61K 8/73; A61K 8/731; A61K 8/463
See application file for complete search history.

(56) References Cited

U.S. PATENT DOCUMENTS

| | | |
|---|---|---|
| 3,538,230 A | 11/1970 | Pader et al. |
| 3,862,307 A | 1/1975 | DiGiulio |
| 3,937,807 A | 2/1976 | Haefele |
| 3,959,458 A | 5/1976 | Agricola et al. |
| 3,970,584 A | 7/1976 | Hart et al. |
| 4,051,234 A | 9/1977 | Gieske et al. |
| 4,301,141 A | 11/1981 | Scheller |
| 4,323,552 A | 4/1982 | Schmolka |
| 4,383,987 A | 5/1983 | Kiozpeoplou |
| 5,004,597 A | 4/1991 | Majeti |
| 5,296,215 A | 3/1994 | Burke et al. |
| 5,496,541 A | 3/1996 | Cutler |
| 5,980,869 A | 11/1999 | Sanker et al. |
| 6,113,884 A | 9/2000 | Mirajkar et al. |
| 6,333,024 B1 * | 12/2001 | Masters .................. A61K 8/19 424/49 |
| 6,447,758 B1 | 9/2002 | Carale et al. |
| 6,692,726 B1 * | 2/2004 | Morgan ............... A61K 8/4926 424/49 |
| 2003/0118522 A1 | 6/2003 | Leinen et al. |
| 2006/0134024 A1 | 6/2006 | Trivedi et al. |

FOREIGN PATENT DOCUMENTS

| | | |
|---|---|---|
| CN | 101115506 | 1/2008 |
| EP | 0 867 173 | 9/1998 |
| EP | 2 371 347 | 10/2011 |
| JP | 2007-145740 | 6/2007 |
| JP | 2009-084277 | 4/2009 |
| JP | 2011-213723 | 10/2011 |
| WO | WO 2001/62212 | 3/2001 |
| WO | WO 2001/062212 | 8/2001 |
| WO | WO 01/76547 | 10/2001 |
| WO | WO 04/073669 | 9/2004 |
| WO | WO 2005/023323 | 3/2005 |
| WO | WO 2006/052743 | 5/2006 |
| WO | WO 2007/094891 | 8/2007 |
| WO | WO 2008/145475 | 12/2008 |
| WO | WO 2009/140577 | 11/2009 |

OTHER PUBLICATIONS

International Search Report and the Written Opinion issued in International Application PCT/US2011/054905 dated Sep. 18, 2013.
JP 2011-213723, McNeil-PPC Inc., "Oral Care Compositions," Oct. 27, 2011, English language machine translation of abstract, Espacenet, date obtained: Apr. 10, 2019, 1 Page <https://worldwide.espacenet.com/publicationDetails/biblio?CC=JP&NR=2011213723A&KC=A&FT=D&ND=3&date=20111027&DB=&locale=en_EP>.
WO 01/76547, Henkel KGAA, "Plaque-Controlling Liquid Tooth Cleaning Gel," Oct. 18, 2001, English language machine translation of abstract, Espacenet, date obtained: Apr. 9, 2019, 1 page <https://worldwide.espacenet.com/publicationDetails/biblio?CC=WO&NR=0176547A1&KC=A1&FT=D&ND=3&date=20011018&DB=&locale=en_EP>.

\* cited by examiner

*Primary Examiner* — Lezah Roberts

(57) ABSTRACT

Described herein are oral care compositions comprising a surfactant system; a structuring agent, and a lipophilic agent; and methods of making and using the same.

10 Claims, No Drawings

ORAL CARE COMPOSITIONS

BACKGROUND

Dentifrice flavor, along with other organoleptic properties, is a major factor in consumer selection of brands. Flavor is a strong signal for the perception of freshness, and valued by consumers, but conventional dentifrice formulations may act to impair rather than enhance the flavorings. Mouthfeel is also important, and toothpaste must be formulated to avoid a taste which is soapy, or gritty, or astringent. Formulating a dentifrice with optimal organoleptic properties is difficult, requiring trial and error, and of course the functional properties of the dentifrice to clean the teeth and deliver benefit agents such as fluoride, whiteners, and/or antibacterial agents should be preserved. Despite the many dentifrice products on the market, there remains a need for products having improved organoleptic properties while providing good cleaning and delivery of actives.

SUMMARY

It is now surprisingly discovered that enhancing the foaming properties of the toothpaste, to provide greater foam density and volume, also enhances the flavor of the toothpaste. Flavors of certain compositions interact with certain toothpaste bases to provide enhanced flavor and mouthfeel.

Some embodiments of the present invention provide an oral care composition comprising: a surfactant system comprising: an anionic surfactant; a zwitterionic surfactant; and a nonionic surfactant; a structuring agent; and a lipophilic agent. Further embodiments provide methods of improving the delivery of a lipophilic agent to the oral cavity of a subject in need thereof.

Some embodiments provide a composition comprising greater than about 4%, by weight of a surfactant; a structuring agent; and a lipophilic agent.

DETAILED DESCRIPTION

As used throughout, ranges are used as shorthand for describing each and every value that is within the range. Any value within the range can be selected as the terminus of the range.

All references cited herein are hereby incorporated by reference in their entireties.

In the event of a conflict in a definition in the present disclosure and that of a cited reference, the present disclosure controls.

As used herein, the term "shear thinning" refers to a property in which viscosity decreases with increasing rate of shear stress. Materials that exhibit shear thinning properties are called pseudoplastic.

As used herein, the term "structuring agent" refers to a substance which is able to form by itself, or in combination with another substance, a structured network in an aqueous medium, and provide a $G'/G'' \geq 1$.

As used herein, the term "lipophilic agent" refers to a substance or mixture of substances which is not freely miscible with water but can form an emulsion in the presence of water and a suitable surfactant or mixture of surfactants.

As used herein, the term "foam density" refers to the density of the foam measured at 30 seconds after initiation of foam generation. In some embodiments, foam density is measured in grams/milliliter.

As used herein, the term "foam volume" refers to the volume of foam measured at 30 seconds after initiation of foam generation. In some embodiments, foam volume is measured in milliliters.

As used herein, the term "free water" means the amount of water added to the composition, above the amount which is contributed by the other components of the composition.

In some embodiments, the present invention provides a toothpaste composition comprising: greater than about 4%, by weight, of a surfactant; a structuring agent; and a lipophilic agent.

In some embodiments, the present invention provides an oral care composition comprising: a surfactant system comprising: an anionic surfactant; a zwitterionic surfactant; and a nonionic surfactant; a structuring agent; and a lipophilic agent. Some embodiments further comprise greater than 20%, by weight, free water. In some embodiments, the composition is a toothpaste.

In some embodiments, the structuring agent comprises a gum-type colloidal polymer. In some embodiments, the gum-type colloidal polymer is selected from: agar, agarose, albumin, algae colloid, alginates, alginic acid and salts thereof, amber, ammoniac, amylopectins, arabinans, arabinogalactan, arabinoxylans, asafetida, bdellium, carageenans, casein, chicle, collagen, copal, curdlan, dermatin sulfate, dextrans, cross-linked dextrans, dextrin, emulsan, gelatin, fenugreek, frankincense, furcellarans, galactoglucomannans, galactomannans, gamboge, gellan, gellan gum, glucomannans, glycogens, guar, guar gum, hydroxypropylated guar gums, carboxymethyl guar gum, carboxymethyl(hydroxypropyl) guar gum, hydroxyethyl guar gum, gum arabic, gum elastic, gum ghatti, gum karaya, gum tragancanth (tragacanthin), heparin, hyaluronic acid, India rubber, inulin, karaya gum, keratin sulfate, konjac flour, konjac mannan, labdanum, laminarans, laurdimonium, laxseed saccharide (acidic), levan, locust bean gum, myrrh, okra gum, pectic acids, pectin, polydextrose, polyquaternium-4, polyquaternium-10, polyquaternium-28, protopectins, psyllium seed gum, pullulan, quince seed gum, sodium hyaluronate, raffinose, rhamsan, scleroglucan, sodium alginate, stachylose, starch from rice, corn, potato or wheat, tapioca starch, succinoglycan, tamarind seed gum, trant gum, water-soluble soybean polysaccharide, whelan, xanthan, xanthan gum, xylans, xyloglucans, and a combination of two or more thereof.

In some embodiments, the structuring agent comprises a non-cellulose gum-type colloidal polymer. In further embodiments, the structuring agent is selected from xanthan gum, pectin, a carageenan, and a combination of two or more thereof. In other embodiments, the structuring agent is xanthan gum.

In some embodiments, the lipophilic agent comprises a mixture of flavor components. In other embodiments, the lipophilic agent has a partition coefficient (octane-water) with an overall log P value of greater than about 1.5. Yet further embodiments provide compositions wherein the lipophilic agent has a partition coefficient (octane-water) with an overall log P value of from about 1.5 to about 4. In some embodiments, the lipophilic agent has a partition coefficient (octane-water) with an overall log P value of about 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or about 4.0.

In some embodiments, the lipophilic agent comprises a flavor component, which may itself comprise a mixture of several materials (e.g. flavoring agents).

Flavoring agents which are suitable for use in the compositions of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

In some embodiments, the compositions further comprise greater than about 15%, by weight, free water. Some embodiments comprise from about 15 to about 40%, by weight, free water. Some embodiments comprise from about 20 to about 35%, by weight, free water. Other embodiments comprise from about 24 to about 32%, by weight, free water. Still further embodiments comprise from about 27 to about 29%, by weight, free water. Some embodiments comprise about 28%, by weight, free water.

In some embodiments, further comprise a humectant. In some embodiments, the humectant also imparts desirable sweetness or flavor to the composition. Some embodiments provide compositions comprising from about 15% to about 70%, by weight, of a humectant. Some embodiments comprise from about 20% to about 60%, by weight, of a humectant. Other embodiments comprise from about 25 to about 50%, by weight, of a humectant. Further embodiments comprise from about 30 to about 40%, by weight, of a humectant. Yet other embodiments comprise from about 32 to about 37%, by weight, of a humectant. While other embodiments comprise about 34%, by weight, of a humectant. Other embodiments comprise about 35%, by weight, of a humectant. In some embodiments, the humectant is present at a concentration of about 34.7%, by weight, of the composition.

Suitable humectants include, but are not limited to, edible polyhydric alcohols such as glycerin, sorbitol, xylitol, propylene glycol as well as other polyols and mixtures thereof. Mixtures of glycerin and sorbitol may be used in certain embodiments as the humectant component of the toothpaste compositions herein.

Some embodiments, provide compositions wherein the surfactant system comprises: from about 0.5 to about 3%, by weight, of an anionic surfactant; from about 0.2 to about 3%, by weight, of a zwitterionic surfactant; and from about 1 to about 3%, by weight, of a nonionic surfactant. In some embodiments, the composition comprises: from about 0.1 to about 2%, by weight, of a structuring agent; from about 1 to about 3%, by weight, of a lipophilic agent; and from about 20 to about 40%, by weight, free water.

Surfactants suitable for use in the compositions of the present invention are those which are reasonably stable throughout a wide pH range, and comprise anionic, nonionic and zwitterionic surfactants. Examples of suitable surfactants are described more fully, for example, in U.S. Pat. No. 3,959,458, to Agricola et al.; U.S. Pat. No. 3,937,807, to Haefele; and U.S. Pat. No. 4,051,234, to Gieske et al., which are incorporated herein by reference. Without being bound by theory, it is believed that the interaction of three types of surfactants allows formation of an emulsion system which results in production of a relatively structured, dense and stable foam.

Anionic surfactants are usually soluble salts of acids having long aliphatic chains, for example sulfate salts having long alkyl chains, e.g., the water-soluble salts of alkyl sulfates having about 10 to about 18 carbon atoms in the alkyl radical, and the water-soluble salts of sulfonated esters of fatty acids having about 10 to about 18 carbon atoms. Sodium lauryl sulfate, sodium lauroyl sarcosinate, sodium cocoyl methyl isethionate and sodium coconut monoglyceride sulfonates are examples of anionic surfactants of this type. Mixtures of anionic surfactants may also be utilized. In a some embodiments, the anionic surfactant comprises sodium lauryl sulfate.

Zwitterionic surfactants useful in the present invention can be broadly described as derivatives of aliphatic quaternary ammonium, phosphomium, and sulfonium compounds, in which the aliphatic radicals can be straight chain or branched, and wherein one of the aliphatic substituents contains about 8 to about 18 carbon atoms and one contains an anionic water-solubilizing group, e.g., carboxy, sulfonate, sulfate, phosphate or phosphonate. Mixtures of zwitterionic surfactants may also be utilized. In some embodiments, the zwitterionic surfactant comprises a betaine, e.g., cocamidopropyl betaine.

Nonionic surfactants suitable for use in the compositions of the present invention are generally produced by the condensation of alkylene oxide groups (hydrophilic in nature) with an organic hydrophobic compound which may be aliphatic or alkylaromatic in nature, for example polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. In some embodiments, the nonionic surfactant comprises a block copolymer based on ethylene oxide and propylene oxide, e.g., a poloxamer. Poloxamers are nonionic triblock copolymers composed of a central hydrophobic chain of polyoxypropylene (poly(propylene oxide)) flanked by two hydrophilic chains of polyoxyethylene (poly(ethylene oxide)). Poloxamers are also known by the trade name Pluronic®. In some embodiments, the nonionic surfactant is poloxamer 407, also known by the BASF trade name Pluronic® F127.

In some embodiments, the compositions comprise from about 1 to about 10%, by weight, of a surfactant system. In some embodiments, the compositions comprise from about 2 to about 8%, by weight, of a surfactant system. In some embodiments, the compositions comprise from about 3 to about 6%, by weight, of a surfactant system. In some embodiments, the compositions comprise from about 4 to about 5%, by weight, of a surfactant system. In some embodiments, the compositions comprise about 4.25%, by weight, of a surfactant system.

Some embodiments provide a composition comprising: about 1.5%, by weight of an anionic surfactant; about 0.75%, by weight, of a zwitterionic surfactant; about 2%, by weight, of a nonionic surfactant; about 0.85%, by weight, of a structuring agent; about 1.5%, by weight, of a lipophilic agent; and about 28%, by weight, free water.

In some embodiments, the lipophilic agent, surfactant system and aqueous components are capable of forming an emulsion.

Some embodiments provide a composition further comprising a fluoride ion source. In some embodiments, the fluoride ion source is selected from: stannous fluoride, sodium fluoride, potassium fluoride, sodium monofluorophosphate, sodium fluorosilicate, ammonium fluorosilicate, amine fluoride, ammonium fluoride, and a combination of two or more thereof. In some embodiments, the fluoride ion source comprises sodium fluoride.

In some embodiments, the fluoride ion source is present at a concentration effective to provide about 25 to about 25,000 ppm. In other embodiments, the fluoride ion source is present at a concentration effective to provide about 750 to about 2,000 ppm. Yet further embodiments provide compositions wherein the fluoride ion source is present at a concentration of from about 0.05 to about 0.5%, by weight. Still other embodiments provide compositions wherein the fluoride ion source is present at a concentration of from about 0.1 to about 0.3%, by weight. Further embodiments provide compositions wherein the fluoride ion source is present at a concentration of from about 0.2 to about 0.25%, by weight. Some embodiments provide compositions wherein the fluoride ion source is present at a concentration of about 0.24%, by weight.

In some embodiments, the compositions further comprise an abrasive. Some embodiments provide a combination of abrasives. Some embodiments include a combination of harder and softer materials to clean and polish the teeth. Some embodiments comprise silica abrasives such as precipitated silicas having a mean particle size of up to about 20 microns, such as Zeodent® 115® or 119®, marketed by J. M. Huber. Other useful abrasives also include sodium metaphosphate, potassium metaphosphate, aluminum silicate, calcined alumina, bentonite or other siliceous materials, or combinations thereof. In some embodiments, the silica abrasive can be a silica gel, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co., Davison Chemical Division.

In some embodiments, the silica abrasive comprises colloidal particles having an average particle size of from about 3 to about 15 microns. In some embodiments, the silica abrasive comprises colloidal particles having an average particle size of from about 4 to about 12 microns. In some embodiments, the silica abrasive comprises colloidal particles having an average particle size of from about 5 to about 10 microns. In some embodiments, the silica abrasive comprises colloidal particles having an average particle size of about 4 to about 8 microns. In some embodiments, the abrasive is present at a concentration of from about 10 to about 60%, by weight, of the composition. In some embodiments, the abrasive is present at a concentration of from about 15 to about 45%, by weight, of the composition. In some embodiments, the abrasive is present at a concentration of from about 20 to about 30%, by weight, of the composition. In some embodiments, the abrasive is present at a concentration of from about 20 to about 25%, by weight, of the composition. In some embodiments, the abrasive is present at a concentration of from about 21 to about 22%, by weight, of the composition.

In some embodiments, the abrasive comprises a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate. Alternatively, calcium carbonate, and in particular precipitated calcium carbonate, may be employed as an abrasive.

In some embodiments, the compositions of the present invention may include an antibacterial agent, e.g. triclosan. In some embodiments, the triclosan is present at a concentration of about 0.3%, by weight, of the composition.

In some embodiments, the compositions comprise a polyoxyethylene (e.g. polyethylene glycol). The polyoxyethylenes suitable for use with the compositions described herein will have a molecular weight of about 200,000 to about 7,000,000. In some embodiments the molecular weight will be about 600,000 to about 2,000,000 and in another embodiment about 800,000 to about 1,000,000. In some embodiments, the polyoxyethylene is present at a concentration of from about 1 to about 10%, by weight, of the composition. In some embodiments, the polyoxyethylene is present at a concentration of from about 2 to about 5%, by weight, of the composition. In some embodiments, the polyoxyethylene is present at a concentration of about 3%, by weight, of the composition.

Another group of agents suitable for use in the compositions of the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least about 1.0 wt. % pyrophosphate ions, about 1.5 wt. % to about 6 wt. %, about 3.5 wt. % to about 6 wt. % of such ions.

The compositions described herein also optionally include one or more polymers, such as polyvinylmethyl ether/maleic acid copolymers, and polysaccharides in addition to the polysaccharide gums discussed above. Acidic polymers, for example polyacrylate gels, may be provided in the form of their free acids or partially or fully neutralized water soluble alkali metal (e.g., potassium and sodium) or ammonium salts. Certain embodiments include about 1:4 to about 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000. These copolymers are available for example as Gantrez AN 139 (M.W. 500,000), AN 119 (M.W. 250,000) and S-97 Pharmaceutical Grade (M.W. 70,000), of GAF Chemicals Corporation.

In addition to the above described components, some embodiments of this invention can contain a variety of optional dentifrice ingredients including, but not limited to, adhesives, additional flavoring agents, sweetening agents, antiplaque agents, additional abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele.

In some embodiments, the compositions of the present invention generate a foam during use. In some embodiments, the foam is generated during brushing. In some embodiments, the foam comprises a matrix containing the lipophilic agent. In some embodiments, the foam has an average density greater than about 0.05 g/mL. In some embodiments, the foam has an average density of from about 0.05 to about 0.2 g/mL. In some embodiments, the foam has an average density of from about 0.10 to about 0.15 g/mL. In some embodiments, the foam has an average density of from about 0.11 to about 0.14 g/mL.

In some embodiments, the foam volume is greater than about 100 mL. In some embodiments, the foam volume is about 500 mL. In some embodiments, the foam volume is from about 100 to about 500 mL. In other embodiments, the foam volume is from about 125 to about 475 mL. In other embodiments, the foam volume is from about 150 to about 450 mL. In further embodiments, the foam volume is from about 175 to about 425 mL. Still other embodiments provide compositions having a foam volume of from about 200 to 400 mL. In some embodiments, the foam volume is from about 225 to about 375 mL. In some embodiments, the foam volume is from about 250 to about 350 mL. In some embodiments, the foam volume is from about 275 to about 325 mL.

Some embodiments provide a method of improving the delivery of a lipophilic agent to the oral cavity comprising contacting an oral cavity surface of a subject in need thereof with a composition according to any preceding claim.

In some embodiments, the improved delivery of the lipophilic agent results in enhanced cooling and/or flavor perception by the user.

Other embodiments provide a method of inhibiting or reducing the accumulation of plaque, reducing levels of acid producing (cariogenic) bacteria, remineralizing teeth, and inhibiting or reducing gingivitis. Some embodiments also encompass methods for cleaning the oral cavity and providing improved methods of promoting oral health and/or systemic health, including cardiovascular health, e.g., by reducing potential for systemic infection via the oral tissues.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Example 1

The foaming properties of a base formulation are tested with systematic variation of different ingredients to determine the impact of different ingredients on foam density and volume.

Foam volume and foam density are measured using a SITA Foam Tester R-2000, available from SITA Messtechnik GmbH. Foam is generated from a slurry sample of toothpaste and water, in a 1:4 ratio, under controlled conditions, using controlled amounts of materials. Foam volume is the observed amount of foam generated from a sample at a time that is 30 seconds after the foam generation is initiated, i.e. after the stirring rod begins moving. Foam density is the volume of liquid converted to foam divided into the mass of the liquid converted to foam.

Example 2

Table 1 (below) describes the formulae of an exemplary composition of the present invention (Composition A) and a commercially available toothpaste (Comparative Example I). Both lab and sensory testing results validate that Composition A exhibits higher foam volume and foam density relative to a commercially available toothpaste having a similar formulation.

TABLE 1

| Ingredient | Composition A | Comparative Ex. I |
| --- | --- | --- |
| Sorbitol | 34.7 | 56.44 |
| Water | 28.04 | 12.24 |
| Zeodent 114 | 11.25 | 10 |
| Zeodent 105 | 10 | 10 |

TABLE 1-continued

| Ingredient | Composition A | Comparative Ex. I |
| --- | --- | --- |
| Polyethylene glycol | 3 | 3 |
| Zeodent 165 | 2.75 | 2.75 |
| Sodium lauryl sulfate | 1.5 | 1.5 |
| Cocoamidopropyl betaine | 0.75 | 1.25 |
| Poloxamer 407 | 2 | — |
| Flavor 1 | — | 1.15 |
| Flavor 2 | 1.45 | — |
| Sodium CMC | — | 0.65 |
| Xanthan | 0.85 | — |
| TSPP | 0.5 | 0.5 |
| Sodium saccharin | 0.4 | 0.27 |
| Sodium fluoride | 0.243 | 0.243 |
| FD&C Blue No. 1 | 0.01 | 0.005 |
| Colorant | 0.6 | — |

Results of a comparative test indicated that Composition A produced a foam having greater foam density and foam volume than the foam produced by Comparative Example I. Mid-infrared spectroscopy analysis of the foam shows that the denser foam of Composition A retains more sodium lauryl sulfate (SLS) in the foam portion of the toothpaste slurry compared to that retained in the foam of Comparative Example I, i.e., Composition A has more SLS in the foam portion than the liquid portion of the toothpaste slurry, while Comparative Example I has more SLS in the liquid portion. The better retention of SLS in the denser foam helps retain flavor better in the foam, leading to improved flavor and cooling perception during use.

Example 3

Three flavors of the prototype product and one commercial benchmark product are tested in a consumer home use test involving approximately 150 respondents, 18-45 years of age, 70% female, 30% male, pre-screened for medical or dental issues or industry affiliations which could bias results. The consumers use each product for three days and respond to a questionnaire, and the data is analyzed.

Most consumers find the amount and thickness of foam in the prototypes, which was considerably higher than in the existing commercial formulations, to be about right, although a few feel it is too much.

TABLE 2

| | Composition A | Comparative Ex. II |
| --- | --- | --- |
| Amount of foam Too Much % | 22% | 15% |
| Thickness of foam Too Much % | 15% | 5% |

Table 2 (above) describes the results of a consumer test which compared an exemplary composition of the present invention to a commercially available toothpaste, which is similarly formulated, but does not include the inventive combination of elements described herein.

The consumers are also asked to rate the flavor attributes of the formulations on nine point scales (nine boxes from 9 "like extremely" to 1 "dislike extremely", results given as percent checking top two boxes (T2B) "like extremely" or "like very much") and on five point scales (five boxes from 5 "much too strong/minty/cooling" to 3 "just about right" to 1 "much too weak/not at all minty/cooling), versus two commercial formulations.

TABLE 3

|  | Composition A | Comparative Ex. I | Comparative Ex. II |
|---|---|---|---|
| Flavor strength liking (T2B %) | 52% | 48% | 38% |
| (Mean) | 7.0 | 6.8 | 5.8 |
| Just about Right % | 67% | 62% | 55% |
| Mintiness liking (T2B %) | 45% | 45% | 28% |
| (Mean) | 6.7 | 6.6 | 5.7 |
| Just about Right % | 62% | 61% | 51% |
| Cooling liking (T2B %) | 49% | 43% | 39% |
| (Mean) | 6.9 | 6.8 | 6.5 |
| Just about Right % | 70% | 65% | 62% |

The consumers are also asked to rate the flavor attributes of the formulations on nine point scales (nine boxes from 9 "like extremely" to 1 "dislike extremely", results given as percent. The results described in Table 3 (above) show that an exemplary composition of the present invention provided enhanced flavor and consumer appeal.

As those skilled in the art will appreciate, numerous changes and modifications may be made to the embodiments described herein without departing from the spirit of the invention. It is intended that all such variations fall within the scope of the appended claims.

What is claimed is:

1. A foaming oral care composition for enhancing flavor comprising:
    a surfactant system comprising:
        an anionic surfactant comprising sodium lauryl sulfate present in an amount of about 0.5 to about 3%, by weight;
        a zwitterionic surfactant comprising cocamidopropyl betaine in an amount of about 0.2 to about 3%, by weight; and
        a nonionic surfactant comprising poloxamer 407 in an amount of about 1 to about 3%, by weight;
    a structuring agent which is xanthan gum in an amount of 0.85%, by weight;
    a lipophilic agent comprising a mixture of flavor components in an amount of about 1 to about 3%, by weight;
    tetrasodium pyrophosphate; and
    from 24% to 32%, by weight, free water,
    a fluoride ion source selected from: stannous fluoride, sodium fluoride, potassium fluoride, sodium monofluorophosphate, sodium fluoro silicate, ammonium fluorosilicate, amine fluoride, ammonium fluoride, and a combination of two or more thereof,
    wherein the composition does not contain a cellulose colloidal polymer and wherein the composition is a single phase toothpaste.

2. The composition of claim 1 wherein the lipophilic agent has a partition coefficient (octane-water) with an overall log P value of greater than about 1.5.

3. The composition of claim 1, comprising:
    about 1.5%, by weight, of an anionic surfactant;
    about 0.75%, by weight, of a zwitterionic surfactant;
    about 2%, by weight, of a nonionic surfactant;
    0.85%, by weight, of a structuring agent;
    about 1.5%, by weight, of a lipophilic agent; and
    about 28%, by weight, free water.

4. The composition of claim 1 wherein the lipophilic agent, surfactant system and aqueous components are capable of forming an emulsion.

5. The composition of claim 1, wherein said foam comprises a matrix containing said lipophilic agent.

6. The composition of claim 1, wherein said foam has a volume greater than about 100 mL.

7. A method of improving the delivery of a lipophilic agent to the oral cavity comprising contacting an oral cavity surface of a subject in need thereof with a composition according to claim 1.

8. The composition of claim 1, wherein the fluoride ion source comprises sodium fluoride.

9. The composition of claim 1, further comprising a silica abrasive.

10. The composition of claim 1, wherein the tetrasodium pyrophosphate is present in an amount of about 0.5% by weight.

* * * * *